(12) United States Patent
Latorre Martinez et al.

(10) Patent No.: US 11,667,747 B2
(45) Date of Patent: Jun. 6, 2023

(54) BINDERS CONTAINING SECONDARY AMINE GROUPS, BASED ON CYCLIC ETHERS

(71) Applicant: Covestro Intellectual Property GmbH & Co. KG, Leverkusen (DE)

(72) Inventors: Irene Cristina Latorre Martinez, Leverkusen (DE); Dorota Greszta-Franz, Solingen (DE); Raul Pires, Cologne (DE); Nusret Yuva, Burscheid (DE); Magdalena Fluegel, Cologne (DE); Andreas Hecking, Langenfeld (DE); Florian Golling, Düsseldorf (DE)

(73) Assignee: Covestro Intellectual Property GmbH & Co. KG, Leverkusen (DE)

( * ) Notice: Subject to any disclaimer, the term of this patent is extended or adjusted under 35 U.S.C. 154(b) by 0 days.

(21) Appl. No.: 17/432,132

(22) PCT Filed: Mar. 19, 2020

(86) PCT No.: PCT/EP2020/057586
§ 371 (c)(1),
(2) Date: Aug. 19, 2021

(87) PCT Pub. No.: WO2020/188024
PCT Pub. Date: Sep. 24, 2020

(65) Prior Publication Data
US 2022/0144998 A1    May 12, 2022

(30) Foreign Application Priority Data
Mar. 19, 2019 (EP) .................................... 19163663

(51) Int. Cl.
*C08G 18/38* (2006.01)
*C07C 227/18* (2006.01)
*C09D 175/06* (2006.01)

(52) U.S. Cl.
CPC ........ *C08G 18/3821* (2013.01); *C07C 227/18* (2013.01); *C09D 175/06* (2013.01); *C08G 2150/00* (2013.01)

(58) Field of Classification Search
None
See application file for complete search history.

(56) References Cited

U.S. PATENT DOCUMENTS

| | | | |
|---|---|---|---|
| 3,072,607 A * | 1/1963 | Fisch | C08G 75/06 549/59 |
| 5,126,170 A | 6/1992 | Zwiener et al. | |
| 5,214,086 A | 5/1993 | Mormile et al. | |
| 5,243,012 A | 9/1993 | Wicks et al. | |
| 5,364,955 A | 11/1994 | Zwiener et al. | |
| 5,412,056 A | 5/1995 | Zwiener et al. | |
| 5,559,204 A | 9/1996 | Squiller et al. | |
| 5,623,045 A | 4/1997 | Zwiener et al. | |
| 7,253,252 B2 * | 8/2007 | Kohler | C07C 229/24 528/61 |
| 10,125,290 B2 | 11/2018 | Flosbach et al. | |
| 10,385,231 B2 | 8/2019 | Enkisch-Krug et al. | |
| 10,968,165 B2 * | 4/2021 | Greszta-Franz | C07C 229/24 |
| 11,230,522 B2 * | 1/2022 | Greszta-Franz | C07C 227/40 |

FOREIGN PATENT DOCUMENTS

| | | | |
|---|---|---|---|
| CA | 2048444 A1 | | 2/1992 |
| DE | 1113565 | * | 9/1961 |
| DE | 19701835 A1 | | 7/1998 |
| EP | 0667362 A1 | | 8/1995 |
| EP | 0893458 A1 | | 1/1999 |
| EP | 3098247 A1 | | 11/2016 |
| EP | 3699218 A1 | | 8/2020 |
| EP | 3699219 A1 | | 8/2020 |

OTHER PUBLICATIONS

Houben-Weyl, Meth. d. Org. Chemie vol. 11/1, 272 (1957).
Usp. Khim. 1969, 38, 1933.
International Search Report, PCT/EP2020/057586, dated Jun. 24, 2020, Authorized officer: Martin Bergmeier.

* cited by examiner

*Primary Examiner* — Tae H Yoon
(74) *Attorney, Agent, or Firm* — John E. Mrozinski, Jr.; Richard P. Bender

(57) ABSTRACT

The present invention relates to a process for producing polyaspartic ester compositions by reacting cyclic ethers bearing primary amino and/or primary aminoalkyl groups with fumaric and/or maleic esters, to the polyaspartic ester compositions thus obtainable, and to the use thereof in two-component coating compositions.

20 Claims, No Drawings

BINDERS CONTAINING SECONDARY AMINE GROUPS, BASED ON CYCLIC ETHERS

CROSS-REFERENCE TO RELATED APPLICATION

This application is a national stage application under 35 U.S.C. § 371 of PCT/EP2020/057586, filed Mar. 19, 2020, which claims the benefit of European Application No. 19163663.8, filed Mar. 19, 2019, each of which is incorporated herein by reference.

FIELD

The present invention relates to a process for producing polyaspartic ester compositions by reacting cyclic ethers bearing primary amino and/or primary aminoalkyl groups with fumaric and/or maleic esters, to the polyaspartic ester compositions thus obtainable, and to the use thereof in two-component coating compositions.

BACKGROUND

Two-component (2C) coating compositions comprising, as binder, a polyisocyanate component in combination with a reactive component that is reactive toward isocyanate groups, in particular a polyhydroxyl component, have long been known. They are suitable for the production of high-quality coatings that can be tailored to make them hard, elastic, resistant to abrasion and, above all, weather-resistant.

Within this 2C polyurethane coating technology, certain ester-containing secondary polyamines have become established in recent years, the so-called polyaspartic esters or polyaspartates, which, in combination with paint polyisocyanates, are particularly suitable as binders in low-solvent or solvent-free (high-solids) coating compositions and allow rapid curing of the coatings at low temperatures. The use in 2C coating compositions of polyaspartate esters either alone or in a mixture with further components that are reactive toward isocyanate groups is described for example in EP0403921, EP0639628, EP0667362, EP0689881, U.S. Pat. No. 5,214,086, EP0699696, EP0596360, EP0893458, DE19701835, EP0470461, WO15130501, WO15130502 and U.S. Pat. No. 5,243,012.

The preparation of amino-functional aspartic esters is known per se. The synthesis is carried out through addition of primary polyamines to an activated carbon-carbon double bond of vinylogous carbonyl compounds, as present for example in maleic or fumaric esters, which is adequately described in the literature (Houben-Weyl, Meth. d. Org. Chemie vol. 11/1, 272 (1957), Usp. Khim. 1969, 38, 1933). In the commercially available polyaspartic esters, maleic ester is used as the vinylogous carbonyl compound.

SUMMARY

The object of the present invention was to provide coating compositions based on polyaspartic esters that result in coatings having substantially improved solvent resistance compared to coatings based on polyaspartic ester-containing coating compositions known from the prior art.

It has surprisingly been found that this object is achieved by using polyaspartic ester compositions obtainable by reacting cyclic ethers bearing primary amino and/or primary aminoalkyl groups with fumaric and/or maleic esters.

EP 141 062 describes the reaction of oxetanes and tetrahydrofurans bearing primary amino groups with isocyanates to afford prepolymers that are processed further into elastomers.

Polyaspartic ester compositions based on cyclic ethers bearing primary amino and/or primary aminoalkyl groups, and the use thereof in coating compositions for producing solvent-stable coatings, are not known from the prior art.

DETAILED DESCRIPTION

The present invention provides compositions A1 comprising or consisting of one or more polyaspartic esters of the general formula (I)

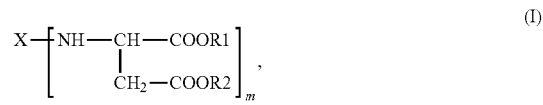

in which

X is an m-valent organic radical that can be obtained by removing the primary amino groups from corresponding cyclic ethers, said ethers being monocycles or fused bicycles based on monocyclic ethers and which on at least 2 of the ring carbon atoms bear a group selected from primary amino group and aliphatically attached primary amino group, where R1 and R2 are identical or different organic radicals each having 1 to 18 carbon atoms and m is an integer >1, and optionally one or more polyaspartic esters having a primary amino group of the general formula (II)

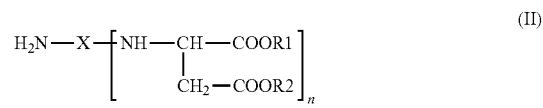

in which n is m−1 and

X and the radicals R1 and R2 are as defined above,

R1 and R2 in formula I and II are preferably identical or different alkyl radicals each having 1 to 18 carbon atoms, more preferably identical or different alkyl radicals each having 1 to 8 carbon atoms, and most preferably in each case alkyl radicals such as methyl, ethyl, propyl, isopropyl, butyl or isobutyl radicals. Most preferred is ethyl.

The cyclic ethers that on at least 2 of the ring carbon atoms bear a group selected from primary amino group and aliphatically attached primary amino group, and from which X is derived, are monocycles or bicycles according to the following general formulas III and IV:

Formula III

-continued
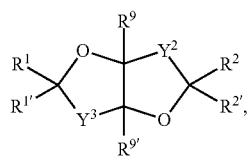
where Y¹ is
Y¹a
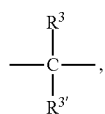
Y¹b
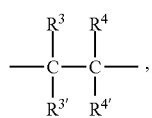
Y¹c
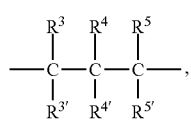
Y¹d
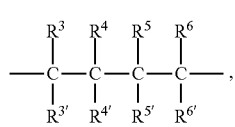
Y¹e
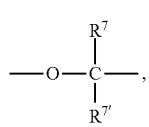
Y¹f
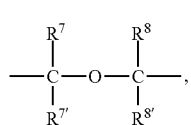
Y¹g
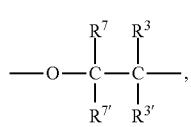
Y¹h
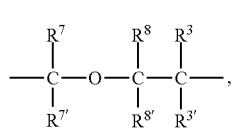
Y¹i
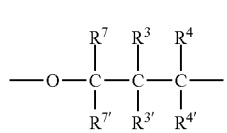
and Y² is
Formula IV
Y²a
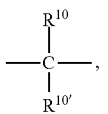
Y²b
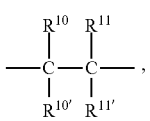
Y²c
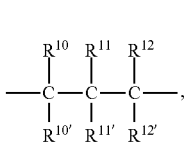
Y²d
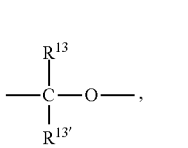
Y²e
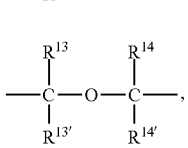
Y²f
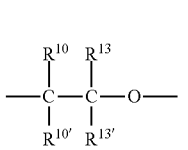
and Y³ is,
Y³a
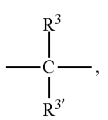
Y³b
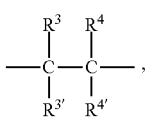
Y³c
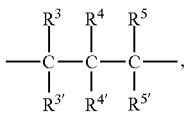
Y³d
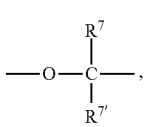
Y³e
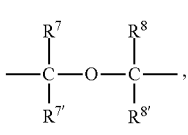

-continued

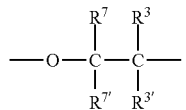
Y³f and

R¹, R², R⁷, R⁸, R¹³, R¹⁴ are independently an alkylene group having 1 to 6 carbon atoms or hydrogen or organic radicals, the latter being saturated or unsaturated, linear or branched, aliphatic or cycloaliphatic or optionally substituted aromatic or araliphatic monovalent radicals having up to 18 carbon atoms, which may optionally contain heteroatoms from the series oxygen, sulfur and nitrogen, the heteroatom-containing radicals including e.g. those that contain functional groups reactive toward isocyanate groups and/or functional groups inert toward isocyanate groups at temperatures up to 100° C. (primary amino groups excepted),
and R³, R⁴, R⁵, R⁶, R¹⁰, R¹¹, R¹² are independently an alkylene group having 1 to 6 carbon atoms or a bond or hydrogen or organic radicals, the latter being saturated or unsaturated, linear or branched, aliphatic or cycloaliphatic or optionally substituted aromatic or araliphatic monovalent radicals having up to 18 carbon atoms, which may optionally contain heteroatoms from the series oxygen, sulfur and nitrogen, the heteroatom-containing radicals including e.g. those that contain functional groups reactive toward isocyanate groups and/or functional groups inert toward isocyanate groups at temperatures up to 100° C. (primary amino groups excepted), where in the case of formula I at least 2 of the radicals R¹ to R⁸ are attached to a $NH_2$ group (i.e. C1 to C6 alkylene group-$NH_2$ (e.g. $CH_2$—$NH_2$) or bond-$NH_2$), and in the case of formula IV at least one of the radicals R¹ to R⁸ is attached to a $NH_2$ group and at least one of the radicals R¹⁰ to R¹⁴ is attached to a $NH_2$ group (i.e. C1 to C6 alkylene group-$NH_2$ (e.g. $CH_2$—$NH_2$) or bond-$NH_2$), and R⁹ and R⁹' are independently H or a methyl radical, and R¹' to R⁸' and R¹⁰' to R¹⁴' are independently hydrogen or organic radicals, the latter being saturated or unsaturated, linear or branched, aliphatic or cycloaliphatic or optionally substituted aromatic or araliphatic monovalent radicals having up to 18 carbon atoms, which may optionally contain heteroatoms from the series oxygen, sulfur and nitrogen, the heteroatom-containing radicals including e.g. those that contain functional groups reactive toward isocyanate groups and/or functional groups inert toward isocyanate groups at temperatures up to 100° C. (primary amino groups excepted).

The alkylene groups having 1 to 6 carbon atoms may be linear or branched, said alkylene groups being preferably $CH_2$, $CH_2$—$CH_2$, $CH_2$—$CH_2$—$CH_2$ or $CH_2$—$CH_2$—$CH_2$—$CH_2$, more preferably $CH_2$.

Where the radicals R¹, R², R³, R⁴, R⁵, R⁶, R⁷, R⁸, R¹⁰, R¹¹, R¹², R¹³, R¹⁴ are hydrogen or organic radicals, they are preferably hydrogen and/or alkyl radicals each having 1 to 8 carbon atoms and very particularly preferably hydrogen and/or alkyl radicals such as methyl, ethyl, propyl, isopropyl, butyl or isobutyl radicals, most preferably hydrogen.

The radicals R¹' to R⁸' and R¹⁰' to R¹⁴ are preferably hydrogen and/or alkyl radicals each having 1 to 8 carbon atoms and very particularly preferably hydrogen and/or alkyl radicals such as methyl, ethyl, propyl, isopropyl, butyl or isobutyl radicals, most preferably hydrogen.

The cyclic ethers bear a group selected from primary amino group and aliphatically attached primary amino group on at least 2 of the ring carbon atoms.

The cyclic ethers of the formula III bear a group selected from primary amino group and aliphatically attached primary amino group preferably on exactly 3 or 2 of the ring carbon atoms, more preferably on exactly 2 of the ring carbon atoms.

The bicyclic ethers of the formula III bear a group selected from primary amino group and aliphatically attached primary amino group preferably on exactly 2 of the ring carbon atoms of one ring and on exactly one of the ring carbon atoms of the second ring. More preferably, each of the two rings bears on exactly one ring carbon atom a group selected from primary amino group and aliphatically attached primary amino group.

In cases where exactly 3 ring carbon atoms bear a group selected from primary amino group and aliphatically attached primary amino group, m in formulas I and II has the value 3. In cases where exactly 2 ring carbon atoms bear such a group, m in formulas I and II has the value 2.

Preferred embodiments of the formula III:

In formula III, Y¹ is preferably i) Y¹a, R¹ and R² are $CH_2$,
and R¹', R²', R³, and R³' are independently organic radicals having up to 18 carbon atoms as defined above or H, preferably alkyl radicals having 1 to 8 carbon atoms or H, ii) Y¹b, 2 of the radicals R¹ to R⁴ are $CH_2$,
and the remaining two of these radicals and also R¹' to R⁴' are independently organic radicals having up to 18 carbon atoms as defined above or H, preferably alkyl radicals having 1 to 8 carbon atoms or H,
or R³ and R⁴ are a bond,
and R¹, R¹', R², R²', R³', and R⁴' are independently organic radicals having up to 18 carbon atoms as defined above or H, preferably alkyl radicals having 1 to 8 carbon atoms or H, iii) Y¹c, 2 of the radicals R¹, R², R³, R⁵ are $CH_2$,
and the remaining two of these radicals and also R¹' to R⁵' and R⁴ are independently organic radicals having up to 18 carbon atoms as defined above or H, preferably alkyl radicals having 1 to 8 carbon atoms or H,
or R³ and R⁴ are a bond,
and R¹, R², R⁵ and also R¹' to R⁵' are independently organic radicals having up to 18 carbon atoms as defined above or H, preferably alkyl radicals having 1 to 8 carbon atoms or H,
or R³ and R⁵ are a bond,
and R¹, R², R⁴ and also R¹' to R⁵' are independently organic radicals having up to 18 carbon atoms as defined above or H, preferably alkyl radicals having 1 to 8 carbon atoms or H,
or R¹ is $CH_2$ and R³, R⁴ or R⁵ are a bond,
and the remaining two radicals from R³, R⁴ and R⁵, and also R¹' to R⁵' and R² are independently organic radicals having up to 18 carbon atoms as defined above or H, preferably alkyl radicals having 1 to 8 carbon atoms or H, iv) Y¹d, 2 of the radicals R¹, R², R³, R⁶ are $CH_2$,
and the remaining two of these radicals and also R⁴, R⁵, and R¹' to R⁶' are independently organic radicals having up to 18 carbon atoms as defined above or H, preferably alkyl radicals having 1 to 8 carbon atoms or H, or $R^3$ and $R^6$ are a bond, and $R^1$, $R^2$, $R^4$, $R^5$ and $R^{1'}$ to $R^{6'}$ are independently organic radicals having up to 18 carbon atoms as defined above or H, preferably alkyl radicals having 1 to 8 carbon atoms or H, or $R^1$ is $CH_2$ and $R^3$ or $R^6$ is a bond, and the remaining radical from $R^3$ and $R^6$, and also $R^{1'}$ to $R^{5'}$ and $R^2$ are independently organic radicals having up to 18 carbon atoms as defined above or H, preferably alkyl radicals having 1 to 8 carbon atoms or H, v) $Y^1e$, 2 of the radicals $R^1$, $R^2$, $R^7$ are $CH_2$, and the remaining one of these 3 radicals and also $R^{1'}$, $R^{2'}$, and $R^{7'}$ are independently organic radicals having up to 18 carbon atoms as defined above or H, preferably alkyl radicals having 1 to 8 carbon atoms or H, vi) $Y^1f$, 2 of the radicals $R^1$, $R^2$, $R^7$, $R^8$ are $CH_2$, and the remaining two of these radicals and also $R^{1'}$, $R^{2'}$, $R^{7'}$, and $R^{8'}$ are independently organic radicals having up to 18 carbon atoms as defined above or H, preferably alkyl radicals having 1 to 8 carbon atoms or H, vii) $Y^1g$, 2 of the radicals $R^1$, $R^2$, $R^3$, $R^7$ are $CH_2$, and the remaining two of these radicals and also $R^{1'}$, $R^{2'}$, $R^{3'}$, and $R^{7'}$ are independently organic radicals having up to 18 carbon atoms as defined above or H, preferably alkyl radicals having 1 to 8 carbon atoms or H, or $R^1$ is $CH_2$ and $R^3$ is a bond, and $R^2$, $R^7$, $R^{1'}$, $R^{2'}$, $R^{3'}$, and $R^{7'}$ are independently organic radicals having up to 18 carbon atoms as defined above or H, preferably alkyl radicals having 1 to 8 carbon atoms or H, viii) $Y^1h$, 2 of the radicals $R^1$, $R^2$, $R^3$, $R^7$, $R^8$ are $CH_2$, and the remaining 3 of these radicals and also $R^{1'}$, $R^{2'}$, $R^{3'}$, $R^{7'}$ and $R^{8'}$ are independently organic radicals having up to 18 carbon atoms as defined above or H, preferably alkyl radicals having 1 to 8 carbon atoms or H, or $R^1$ is $CH_2$ and $R^3$ is a bond, and $R^2$, $R^7$, and $R^8$ and also $R^{1'}$, $R^{2'}$, $R^{3'}$, $R^{7'}$, and $R^{8'}$ are independently organic radicals having up to 18 carbon atoms as defined above or H, preferably alkyl radicals having 1 to 8 carbon atoms or H, ix) $Y^1i$, 2 of the radicals $R^1$, $R^2$, $R^3$, $R^4$, $R^7$ are $CH_2$, and the remaining three of these radicals and also $R^{1'}$, $R^{2'}$, $R^{3'}$, $R^{4'}$, and $R^{7'}$ are independently organic radicals having up to 18 carbon atoms as defined above or H, preferably alkyl radicals having 1 to 8 carbon atoms or H, or $R^1$ is $CH_2$ and $R^3$ or $R^4$ is a bond, and the remaining radical from $R^3$ and $R^4$, and also $R^2$, $R^7$, $R^{1'}$, $R^{2'}$, $R^{3'}$, $R^{4'}$, and $R^{7'}$, are independently organic radicals having up to 18 carbon atoms as defined above or H, preferably alkyl radicals having 1 to 8 carbon atoms or H.

Particularly preferred embodiments of the formula III are the embodiments ii), iii), v), vi), and vii).

Very particularly preferred are embodiments ii) and iii), where ii) Y1 is $Y^1b$, $R^1$ and $R^2$ are $CH_2$, and $R^3$, $R^4$ and also $R^{1'}$ to $R^{4'}$ are independently organic radicals having up to 18 carbon atoms as defined above or H, preferably alkyl radicals having 1 to 8 carbon atoms or H, or $R^3$ and $R^4$ are $CH_2$ or a bond, and $R^1$, $R^2$ and also $R^{1'}$ to $R^{4'}$ are independently organic radicals having up to 18 carbon atoms as defined above or H, preferably alkyl radicals having 1 to 8 carbon atoms or H, and iii) Y1 is $Y^1c$, $R^1$ and $R^2$ are $CH_2$, and $R^3$, $R^4$, $R^5$ and also $R^{1'}$ to $R^{5'}$ are independently organic radicals having up to 18 carbon atoms as defined above or H, preferably alkyl radicals having 1 to 8 carbon atoms or H, or $R^3$ and $R^5$ are $CH_2$ or a bond, and $R^1$, $R^2$, $R^4$ and also $R^{1'}$ to $R^{5'}$ are independently organic radicals having up to 18 carbon atoms as defined above or H, preferably alkyl radicals having 1 to 8 carbon atoms or H.

Most preferred are embodiments ii) and iii), where ii) Y1 is $Y^1b$, $R^1$ and $R^2$ are $CH_2$, and $R^3$, $R^4$ and also $R^{1'}$ to $R^{4'}$ are independently a methyl radical or H, preferably H, or $R^3$ and $R^4$ are $CH_2$ or a bond, and $R^1$, $R^2$ and also $R^{1'}$ to $R^{4'}$ are independently a methyl radical or H, preferably H, and iii) Y1 is $Y^1c$, $R^1$ and $R^2$ are $CH_2$, and $R^3$, $R^4$, $R^5$ and also $R^{1'}$ to $R^{5'}$ are independently a methyl radical or H, preferably H, or $R^3$ and $R^5$ are $CH_2$ or a bond, and $R^1$, $R^2$, $R^4$ and also $R^{1'}$ to $R^{5'}$ are independently a methyl radical or H, preferably H.

Examples of the most preferred compounds of the formula III are oxacyclopentane-2,3-, -2,4-, -2,5- or -3,4-di-methyleneamine or oxacyclohexane-2,3-, -2,4-, -2,5-, -2,6-, -3,4- or -3,5-di-methyleneamine.

Preferred embodiments of the formula IV:

In formula IV, $Y^2$ and $Y^3$ are preferably a) $Y^2a$ and $Y^3a$, $R^2$ is $CH_2$ or $R^{10}$ is $CH_2$ or a bond and $R^1$ is $CH_2$ or $R^3$ is $CH_2$ or a bond, and the remaining radical from $R^2$ and $R^{10}$, the remaining radical from $R^1$ and $R^3$, and also $R^{1'}$, $R^{2'}$, $R^{3'}$, and $R^{10'}$ are independently methyl, ethyl, propyl, isopropyl, butyl or isobutyl radicals or H, preferably H, and $R^9$, $R^{9'}$ are independently $CH_3$ or H, preferably H, b) $Y^2a$ and $Y^3b$, $R^2$ is $CH_2$ or $R^{10}$ is $CH_2$ or a bond and $R^1$ is $CH_2$ or $R^3$ or $R^4$ is $CH_2$ or a bond, and the remaining radical from $R^2$ and $R^{10}$, the remaining radicals from $R^1$, $R^3$, and $R^4$, and also $R^{1'}$, $R^{2'}$, $R^{3'}$, $R^{4'}$, and $R^{10'}$ are independently methyl, ethyl, propyl, isopropyl, butyl or isobutyl radicals or H, preferably H, and $R^9$, $R^{9'}$ are independently $CH_3$ or H, preferably H, c) $Y^2a$ and $Y^3d$, $R^2$ is $CH_2$ or $R^{10}$ is $CH_2$ or a bond and $R^1$ or $R^7$ is $CH_2$, and the remaining radical from $R^2$ and $R^{10}$, the remaining radical from $R^1$ and $R^7$, and also $R^{1'}$, $R^{2'}$, $R^{7'}$, and $R^{10'}$ are independently methyl, ethyl, propyl, isopropyl, butyl or isobutyl radicals or H, preferably H, and $R^9$, $R^{9'}$ are independently $CH_3$ or H, preferably H, d) $Y^2b$ and $Y^3b$, $R^2$ is $CH_2$ or $R^{10}$ or $R^{11}$ is $CH_2$ or a bond and $R^1$ is $CH_2$ or $R^3$ or $R^4$ is $CH_2$ or a bond, and the remaining radicals from $R^2$, $R^{10}$, and $R^{11}$, the remaining radicals from $R^1$, $R^3$, and $R^7$, and also $R^{1'}$, $R^{2'}$, $R^{3'}$, $R^{4'}$, $R^{10'}$, and $R^{11'}$ are independently methyl, ethyl, propyl, isopropyl, butyl or isobutyl radicals or H, preferably H, and $R^9$, $R^{9'}$ are independently $CH_3$ or H, preferably H, e) $Y^2d$ and $Y^3d$, $R^2$ or $R^{13}$ is $CH_2$ and $R^1$ or $R^7$ is $CH_2$, and the remaining radical from $R^2$ and $R^{13}$, the remaining radical from $R^1$ and $R^7$, and also $R^{1'}$, $R^{2'}$, $R^{7'}$, and $R^{13'}$ are independently methyl, ethyl, propyl, isopropyl, butyl or isobutyl radicals or H, preferably H, and $R^9$, $R^{9'}$ are independently $CH_3$ or H, preferably H, f) $Y^2$b and $Y^3$d, $R^2$ is $CH_2$ or $R^{10}$ or $R^{11}$ is $CH_2$ or a bond
or
$R^1$ or $R^7$ is $CH_2$,
and the remaining radicals from $R^2$, $R^{10}$ and $R^{11}$, the remaining radical from $R^1$ and $R^7$, and also $R^{1'}$, $R^{2'}$, $R^{7'}$, $R^{10'}$ and $R^{11}$ are independently methyl, ethyl, propyl, isopropyl, butyl or isobutyl radicals or H, preferably H, and $R^9$, $R^{9'}$ are independently $CH_3$ or H, preferably H.

Particularly preferred embodiments of the formula IV are embodiments a), b), and d). Very particular preferred are embodiments a), b), and d) with the constraint that $R^9$, $R^{9'}$, and the radicals that are not $CH_2$ or a bond are independently methyl radicals or H, preferably H. Most preferred is embodiment a) with the constraint that $R^9$, $R^{9'}$, and the radicals that are not $CH_2$ or a bond are independently methyl radicals or H, preferably H.

Examples of particularly preferred compounds of the formula IV are 3R,3aR,6R,6aR-hexahydrofuro[3,2-b]furan-3,6-diamine, 3R,3aR,6S,6aR-hexahydrofuro[3,2-b]furan-3,6-diamine, 3S,3aR,6S,6aR-hexahydrofuro[3,2-b]furan-3,6-diamine, [3R,3aR,6R,6aR-6-(aminomethyl)-hexahydrofuro[3,2-b]furan-3-yl]methanamine, [3R,3aR,6S,6aR-6-(aminomethyl)-hexahydrofuro[3,2-b]furan-3-yl]methanamine, [3S,3aR,6S,6aR-6-(aminomethyl)-hexahydrofuro[3,2-b]furan-3-yl]methanamine, and mixtures thereof.

Biobased Diamines:

Diamines of the formula III, where $Y^1$ is $Y^1$b, and
2 of the radicals $R^1$ to $R^4$ are $CH_2$,
and the remaining two of these radicals and also $R^{1'}$ to $R^{4'}$ are independently organic radicals having up to 18 carbon atoms as defined above or H, preferably alkyl radicals having 1 to 8 carbon atoms or H,
or $R^3$ and $R^4$ are a bond,
and $R^1$, $R^{1'}$, $R^2$, $R^{2'}$, $R^{3'}$, and $R^{4'}$ are independently organic radicals having up to 18 carbon atoms as defined above or H, preferably alkyl radicals having 1 to 8 carbon atoms or H,
and
diamines of the formula IV, where $Y^2$ and $Y^3$ are $Y^2$a and $Y^3$a,
$R^{10}$ is $CH_2$ or a bond and
$R^3$ is $CH_2$ or a bond,
and $R^1$, $R^2$, $R^{1'}$, $R^{2'}$, $R^{3'}$ and $R^{10'}$ are independently methyl, ethyl, propyl, isopropyl, butyl or isobutyl radicals or H, preferably H, and $R^9$, $R^{9'}$ are independently $CH_3$ or H, preferably H, and, in particular, oxacyclopentane-2,5-di-methyleneamine (bis(aminomethyl)tetrahydrofuran/formula III) and the hexahydrofuro[3,2-b]furan-3,6-diamine or [(aminomethyl)-hexahydrofuro[3,2-b]furan-3-yl]-methanamine stereoisomers mentioned above (formula IV) can be prepared for example from furfural or substituted furfurals, for example 5-hydroxymethylfurfural, or from isosorbide, isomannide or isoidide as starting materials. These starting materials can be obtained from biobased or non-biobased sources.

The term "starting material" means that the substance undergoes chemical transformation during production of the diamines, i.e. is used up.

In the context of the present invention, the term "biobased" is defined as meaning a compound, a material or the like, for example a starting material or a polyamine of the formula III or IV, obtained from renewable sources such as plants, microorganisms, algae or animals or prepared therefrom. Non-biobased compounds and materials are, on the other hand, those obtained or prepared from non-renewable sources. Non-renewable sources include, for example, fossil raw materials formed from dead living organisms in geological prehistory. These include in particular crude oil, lignite, coal, peat, and natural gas. Compounds and materials obtained or prepared from non-renewable sources are defined in the context of the present invention as non-biobased or "synthetically produced".

Biobased starting materials can be obtained directly from the abovementioned renewable sources or can be produced by subsequent reactions from compounds or materials obtained from such sources.

When biobased diamines are used to produce the polyaspartic ester compositions A1 of the invention, this means that these diamines are completely or partly biobased. This depends on the extent to which biobased starting materials are being used in production. In the case of partly biobased diamines, at least one biobased starting material is being used.

The furfural mentioned above or substituted derivatives thereof, such as 5-hydroxymethylfurfural, can be obtained in a biobased manner from pentoses and hexoses, which are in turn obtainable from the fractionation of cellulose, starch or other polysaccharides. The described synthesis is merely one example of a possible synthesis. Any other form of biobased production of furfural or derivatives thereof is of course also possible.

The production of 2,5-bis(aminomethyl)tetrahydrofuran can take place, for example, by chemical conversion of biobased 5-hydroxymethylfurfural via 2,5-furandicarboxylic acid, 2,5-bis(hydroxymethyl)furan, and 2,5-dihydroxymethyl-tetrahydrofuran, or by chemical conversion of biobased furfural via furfuryl alcohol, tetrahydrofurfuryl alcohol, 2-hydroxymethyl-vinylfuran, 2,5-bis(hydroxymethyl)furan, and 2,5-dihydroxymethyl-tetrahydrofuran. These syntheses too are mentioned purely by way of example and should not be understood as definitive.

Isosorbide, isomannide or isoidide can likewise be obtained in a biobased manner, for example from pentoses and hexoses. These sugars are used to produce sorbitol or mannitol, which are in turn dehydrated to isosorbide and isomannide respectively. Isosorbide can also undergo isomerization to isomannide. Isoidide is obtained from the isomerization of isosorbide or isomannide. The syntheses described here are likewise only examples. Any other form of biobased production of isosorbide, isomannide or isoidide is of course also possible.

It should at this point also be made clear that the abovementioned diamines can also be obtained in a non-biobased manner and, as such, can also be used for the production of the polyaspartic ester compositions A1 of the invention.

In one embodiment of the invention, compositions A1 comprising polyaspartic esters correspond to those in which X can be obtained by removing the primary amino groups from cyclic ethers of the type described above that are based on starting materials obtained in a biobased manner.

In a preferred variant of this embodiment, compositions A1 comprising polyaspartic esters compositions A1 correspond to those in which X can be obtained by removing the primary amino groups from cyclic ethers that correspond to
diamines of the formula III, where $Y^1$ is $Y^1$b, and
2 of the radicals $R^1$ to $R^4$ are $CH_2$,
and the remaining two of these radicals and also $R^{1'}$ to $R^{4'}$ are independently organic radicals having up to 18 carbon atoms as defined above or H, preferably alkyl radicals having 1 to 8 carbon atoms or H, or $R^3$ and $R^4$ are a bond, and $R^1$, $R^{1\prime}$, $R^2$, $R^{2\prime}$, $R^{3\prime}$, and $R^{4\prime}$ are independently organic radicals having up to 18 carbon atoms as defined above or H, preferably alkyl radicals having 1 to 8 carbon atoms or H, or diamines of the formula IV, where $Y^2$ and $Y^3$ are $Y^2a$ and $Y^3a$, $R^{10}$ is $CH_2$ or a bond and $R^3$ is $CH_2$ or a bond, and $R^1$, $R^2$, $R^{1\prime}$, $R^{2\prime}$, $R^{3\prime}$ and $R^{10\prime}$ are independently methyl, ethyl, propyl, isopropyl, butyl or isobutyl radicals or H, preferably H, and $R^9$, $R^{9\prime}$ are independently $CH_3$ or H, preferably H, these diamines being based on starting materials that were obtained in a biobased manner.

In a particularly preferred variant of this embodiment, compositions A1 containing polyaspartic esters correspond to those in which X can be obtained by removing the primary amino groups from 3R,3aR,6R,6aR-hexahydrofuro[3,2-b]furan-3,6-diamine, 3R,3aR,6S,6aR-hexahydrofuro[3,2-b]furan-3,6-diamine, [3S,3aR,6S,6aR-hexahydrofuro[3,2-b]furan-3,6-diamine, 3R,3aR,6R,6aR-6-(aminomethyl)-hexahydrofuro[3,2-b]furan-3-yl]-methanamine, [3R,3aR,6S,6aR-6-(aminomethyl)-hexahydrofuro[3,2-b]furan-3-yl]-methanamine, [3S,3aR,6S,6aR-6-(aminomethyl)-hexahydrofuro[3,2-b]furan-3-yl]-methanamine or oxacyclopentane-2,5-di-methyleneamine, these diamines being based on starting materials that were obtained in a biobased manner.

Where the composition A1 comprises one or more polyaspartic esters of the general formula (II), these are present in a proportion of >0%, preferably not less than 0.1% (≥0.1%), more preferably not less than 1% (≥1%), most preferably not less than 4% (≥4%), and preferably not more than 20% (≤20%), more preferably not more than 15% (≤15%), of the area by GC (measured as area % in the gas chromatogram), wherein the sum of the areas by GC of compounds of the two general formulas (I) and (II) is 100%. Any combination of the specified upper and lower limits is possible. All possible combinations are considered disclosed.

The compositions A1 preferably comprise or consist of one or more polyaspartic esters of the general formula (I) and optionally formula (II) that have a platinum-cobalt color index ≤100, more preferably ≤50. The platinum-cobalt color index is measured in accordance with DIN EN ISO 6271: 2016-05.

The present invention also provides a process for producing compositions A1 comprising or consisting of one or more polyaspartic esters of the general formula (I) and optionally formula (II).

Compositions A1 comprising or consisting of one or more polyaspartic esters of the general formula (I) and formula (II) can be prepared by the following process:

Reaction of polyamines of the general formula (V),

where X is an m-valent organic radical, as is obtained by removing the primary amino groups from a corresponding cyclic ether that is a monocycle or polycycle having saturated and/or unsaturated carbon-carbon bonds in the ring(s) and having a primary amino group and/or an aliphatically attached primary amino group on at least 2 of the ring carbon atoms, wherein m is an integer >1, preferably 3, more preferably 2, with compounds of the general formula (VI)

where R1 and R2 are identical or different organic radicals, preferably identical or different alkyl radicals each having 1 to 18 carbon atoms, more preferably identical or different alkyl radicals each having 1 to 8 carbon atoms, very particularly preferably in each case alkyl radicals such as methyl, ethyl, propyl, isopropyl, butyl or isobutyl radicals and most preferably ethyl.

To produce the composition A1 comprising or consisting of one or more polyaspartic esters of the general formula (I) and formula (II), the compounds of the general formula (V) and (VI) are reacted at temperatures between 0° C. and 100° C., preferably 20 to 80° C., and more preferably 20 to 60° C., in a ratio of equivalents of primary amino groups in the compounds of the general formula (V) to C=C double bond equivalents in the compounds of the general formula (VI) of 1:1.2 to 1.2:1, but preferably 1:1.05 to 1.05:1, until the residual content of compounds of the general formula (VI) is from 2 to 15 percent by weight, preferably from 3 to 10 percent by weight.

Compositions A1 that comprise only polyaspartic esters of the general formula (I), but not of the formula (II), can be prepared in analogous manner, but using an excess of compounds of the general formula (VI), i.e. in a ratio of equivalents of primary amino groups in the compounds of the general formula (V) to C=C double bond equivalents in the compounds of the general formula (VI) of 1:10, preferably 1:5, more preferably 1:2.

The process described above may be followed by a distillation step to remove the unreacted portion of the compound of the general formula (VI). Such a procedure is preferred.

Preference is therefore given to compositions A1 comprising or consisting of one or more polyaspartic esters of the general formula (I) and optionally formula (II) in which the proportion of compounds of the formula (VI) is 0.01% to 1.2% by weight (≥0.01% to ≤1.2% by weight), preferably 0.01% to 1% by weight (≥0.01% to ≤10% by weight), more preferably 0.01% to 0.1% by weight (≥0.01% to ≤0.1% by weight), based on the total weight of component A, dialkyl fumarates being preferred.

Suitable conditions during the distillation are a pressure range between 0.01 and 2 mbar and a temperature of the bottom outflow on exiting the distillation apparatus of ≤170° C. and ≥ the temperature resulting from the following formula (VII):

$$T(\text{bottom outflow}) = 27 \times \ln(p) + 150 \quad \text{(VII)}$$

where T(bottom outflow) is the temperature of the bottom outflow in ° C. and p is the pressure in the distillation apparatus in mbar.

Maintaining this pressure range ensures not only that moderate temperatures in the bottom outflow are sufficient for depletion of the dialkyl fumarate content to the desired extent, but that the process remains usable on an industrial scale. At lower pressure, the gas density becomes too low and the necessary apparatus consequently so large that the process becomes economically disadvantageous.

The temperature of the bottom outflow is preferably ≤170° C., but at least 20 K above the temperature resulting from formula (VII); more preferably it is between 20 K and 40 K above the temperature resulting from formula (VII), but not higher than 170° C.

Primary polyamines of the general formula (V) that are used in the process described above correspond to the monocyclic and polycyclic ethers described in the discussion of formulas I and II, including the preferred ranges described therein.

Preferred compounds of the general formula (VI) that are used in the process described above are maleic or fumaric esters of the general formula (VI) in which R1 and R2 are identical or different organic radicals each having 1 to 18 carbon atoms. Preferably, R1 and R2 are independently linear or branched alkyl radicals having 1 to 8 carbon atoms, more preferably they are each alkyl radicals such as methyl, ethyl, propyl, isopropyl, butyl or isobutyl radicals and particularly preferably ethyl.

Examples of compounds of the general formula (VI) include the following compounds: dimethyl maleate, diethyl maleate, di-n-propyl or diisopropyl maleate, di-n-butyl maleate, di-2-ethylhexyl maleate or the corresponding fumaric esters. Very particular preference is given to diethyl maleate.

The present invention also provides the compositions A1 comprising or consisting of polyaspartic esters in a mixture with further polyaspartic esters different from A1 or compositions comprising or consisting of polyaspartic esters (component A2).

These compositions A2 include, for example, the compositions A2.1 described hereinbelow, with which the compositions A1 may be blended within certain limits:

Compositions A2.1 comprising or consisting of one or more polyaspartic esters of the general formula (VIII)

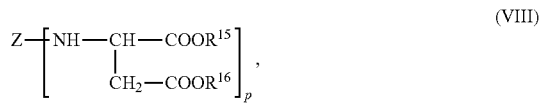

(VIII)

in which

Z is a p-valent organic radical, optionally containing one or more heteroatoms, as can be obtained by removing the primary amino groups from a corresponding polyamine that has (cyclo) aliphatically or araliphatically attached amino groups and is in the molecular weight range from 60 to 6000 g/mol, and which may contain further functional groups reactive toward isocyanate groups and/or functional groups inert toward isocyanate groups at temperatures of up to 100° C., $R^{15}$ and $R^{16}$ are identical or different organic radicals each having 1 to 18 carbon atoms, p is an integer >1, preferably 2, and optionally one or more polyaspartic esters having a primary amino group that are of the general formula (IX)

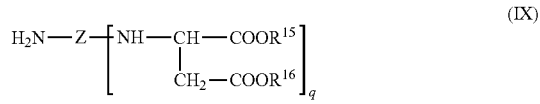

(IX)

in which q is p−1,

Z, radicals $R^{15}$ and $R^{16}$ are as defined above.

Preference is given here to polyaspartic ester-containing compositions A2.1 comprising or consisting of one or more polyaspartic esters of the general formulas (VIII) and optionally (IX) in which $R^{15}$ and $R^{16}$ are identical or different alkyl radicals each having 1 to 18 carbon atoms, preferably identical or different alkyl radicals each having 1 to 8 carbon atoms, and most preferably in each case alkyl radicals such as methyl, ethyl, propyl, isopropyl, butyl or isobutyl radicals. Most preferred is ethyl.

Polyaspartic ester-containing compositions A2.1 are compositions comprising or consisting of one or more polyaspartic esters of the general formulas (VIII) and optionally (IX) in which Z is organic radicals obtained by removing the primary amino groups from a corresponding polyamine having (cyclo) aliphatically or araliphatically attached primary amino groups.

Examples include the following polyamines: ethylenediamine, 1,2-diaminopropane, 1,4-diaminobutane, 1,5-diaminopentane, 2,5-diamino-2,5-dimethylhexane, 1,5-diamino-2-methylpentane (Dytek® A, from DuPont), 1,6-diaminohexane, 2,2,4- and/or 2,4,4-trimethyl-1,6-diaminohexane, 1,11-diaminoundecane, 1,12-diaminododecane or triaminononane, etheramines such as 4,9-dioxadodecane-1,12-diamine, 4,7,10-trioxatridecane-1, 13-diamine or higher-molecular-weight polyether polyamines having aliphatically attached primary amino groups, for example those marketed under the Jeffamine® name by Huntsman. Also employable are aliphatic polycyclic polyamines such as tricyclodecanebismethylamine (TCD diamine) or bis(aminomethyl)norbornanes, aminofunctional siloxanes, for example diaminopropylsiloxane G10 DAS (from Momentive), oleoalkyl-based amines, for example Fentamine from Solvay, dimeric fatty acid diamines such as Priamine from Croda.

Further examples of diamines that may be used are 1-amino-3,3,5-trimethyl-5-aminomethylcyclohexane (IPDA), 2,4- and/or 2,6-hexahydrotolylenediamine (H6-TDA), isopropyl-2,4-diaminocyclohexane and/or isopropyl-2,6-diaminocyclohexane, 1,3-bis(aminomethyl)cyclohexane, 2,4'-, and/or 4,4'-diaminodicyclohexylmethane, 3,3'-dimethyl-4,4'-diaminodicyclohexylmethane (Laromin® C 260, BASF AG), the isomeric diaminodicyclohexylmethanes substituted in the ring with a methyl group (=C-monomethyl-diaminodicyclohexylmethanes), 3(4)-aminomethyl-1-methylcyclohexylamine (AMCA) and also araliphatic diamines such as 1,3-bis(aminomethyl)benzene or m-xylylenediamine.

Preferred amines are: polyether polyamines having aliphatically attached primary amino groups, 1,2-diaminopropane, 1,4-diaminobutane, 1,6-diaminohexane, 1,5-diamino-2-methylpentane, 2,5-diamino-2,5-dimethylhexane, 2,2,4- and/or 2,4,4-trimethyl-1,6-diaminohexane, 1,11-diaminoundecane, 1,12-diaminododecane, 1-amino-3,3,5-trimethyl-5-aminomethylcyclohexane, 2,4- and/or 2,6-hexahydrotolylenediamine, 1,5-diaminopentane, 2,4'- and/or 4,4'-diaminodicyclohexylmethane or 3,3'-dimethyl-4,4'-diaminodicyclohexylmethane. Particular preference is given to 1,2-diaminopropane, 1,4-diaminobutane, 1,5-diaminopentane, 1,6-diaminohexane, 1,5-diamino-2-methylpentane, 2,5-diamino-2,5-dimethylhexane, 2,2,4- and/or 2,4,4-trimethyl-1,6-diaminohexane, 1,11-diaminoundecane, 1,12-diaminododecane, 1-amino-3,3,5-trimethyl-5-aminomethylcyclohexane, 2,4- and/or 2,6-hexahydrotolylenediamine, 2,4'- and/or 4,4'-diaminodicyclohexylmethane or 3,3'-dimethyl-4,4'-diaminodicyclohexylmethane.

Very particularly preferred are 3,3'-dimethyl-4,4'-diaminodicyclohexylmethane, 2,4'- and/or 4,4'-diaminodicyclohexylmethane, and 1,5-diamino-2-methylpentane.

Composition A2.1 can be produced using the amines specified above in analogous manner to the production process described above for composition A1 and which is also disclosed, for example, in EP19158880.5 or EP19158883.9.

For a mixture of composition A1 and A2.1, the following applies:

The proportion of the compounds of the formula VIII or of the formulas VIII and IX (total amount, if compounds of the formula IX are present) in the total weight of the compounds of the formulas I, II (if present), VIII, and IX (if present) is ≤20% by weight, preferably ≤15% by weight, more preferably ≤10% by weight.

The present invention also provides for the use of compositions A1 comprising one or more polyaspartic esters of the general formula (I) and optionally formula (II), optionally in a mixture with further polyaspartic esters or compositions A2 comprising or consisting of polyaspartic esters, in the production of coating compositions, preferably two-component coating compositions (2C coating compositions); it also provides the coating compositions thereby obtainable, for the use thereof in the coating of substrates, the process for coating a substrate, and the substrates thereby obtainable.

The present invention therefore provides coating compositions, preferably two-component coating compositions (2C coating compositions), comprising
a1) at least one polyaspartic ester-containing composition A1,
a2) optionally further polyaspartic esters different from A1 or compositions A2 comprising or consisting of polyaspartic esters,
b) at least one polyisocyanate component B,
c) optionally one or more components C different from A1 and A2 and reactive toward isocyanate groups,
d) optionally auxiliaries and additives (component D).

The preferably two-component coating compositions of the invention comprise at least one polyisocyanate component B.

Suitable polyisocyanate components B are organic polyisocyanates having an average NCO functionality of at least 2 and a molecular weight of at least 140 g/mol. Particularly well suited are unmodified organic polyisocyanates in the molecular weight range from 140 to 300 g/mol, paint polyisocyanates in the molecular weight range from 300 to 1000 g/mol and NCO prepolymers having urethane, urea and/or allophanate groups and a molecular weight above 400 g/mol, or mixtures thereof.

In the context of the invention, the term "paint polyisocyanates" is understood as meaning compounds or mixtures of compounds that can be obtained from simple polyisocyanates by an oligomerization reaction known per se. Examples of suitable oligomerization reactions are carbodiimidization, dimerization, trimerization, biuretization, urea formation, urethanization, allophanatization and/or cyclization with formation of oxadiazine structures. Oligomerization may consist of more than one of the above-mentioned reactions performed simultaneously or in succession.

The "paint polyisocyanates" are preferably biuret polyisocyanates, polyisocyanates containing isocyanurate groups, mixtures of polyisocyanates containing isocyanurate and uretdione groups, polyisocyanates containing urethane and/or allophanate groups, or mixtures of polyisocyanates containing isocyanurate and/or allophanate groups based on simple organic polyisocyanates.

Likewise suitable as polyisocyanate component B are prepolymers containing isocyanate groups that are known per se and based on simple organic polyisocyanates and/or based on paint polyisocyanates on the one hand and organic polyhydroxy compounds having a molecular weight above 300 g/mol on the other hand. Whereas the paint polyisocyanates containing urethane groups are derivatives of low-molecular-weight polyols in the molecular weight range from 62 to 300 g/mol, suitable polyols being, for example, ethylene glycol, propylene glycol, trimethylolpropane, glycerol or mixtures of these alcohols, the prepolymers containing isocyanate groups are prepared using polyhydroxy compounds having a molecular weight above 300 g/mol, preferably above 400 g/mol, more preferably between 400 and 8000 g/mol. Such polyhydroxyl compounds are in particular those having 2 to 6, preferably 2 to 3, hydroxyl groups per molecule and are selected from the group consisting of ether, ester, thioether, carbonate and polyacrylate polyols and mixtures of such polyols.

In the preparation of the prepolymers containing isocyanate groups, the mentioned higher-molecular-weight polyols may also be used in the form of mixtures with the mentioned low-molecular-weight polyols, giving rise directly to mixtures of low-molecular-weight paint polyisocyanates containing urethane groups and higher-molecular-weight NCO prepolymers that are likewise suitable as polyisocyanate component b) of the invention.

For the preparation of the prepolymers containing isocyanate groups or mixtures thereof with paint polyisocyanates, simple organic polyisocyanates of the type mentioned by way of example below or paint polyisocyanates are reacted with higher-molecular-weight hydroxyl compounds or mixtures thereof with low-molecular-weight polyhydroxyl compounds of the type mentioned by way of example, while maintaining an NCO/OH equivalents ratio of 1.1:1 to 40:1, preferably 2:1 to 25:1, with urethane and/or allophanate formation. If using an excess of a distillable simple organic polyisocyanate, this may optionally be removed after the reaction by distillation, with the result that NCO prepolymers containing monomer-free isocyanate groups are present that may likewise be used as polyisocyanate component b).

Examples of suitable simple organic polyisocyanates are 1,4-diisocyanatobutane, 1,5-diisocyanatopentane, 1,6-diisocyanatohexane (HDI), 1,5-diisocyanato-2,2-dimethylpentane, 2,2,4- and 2,4,4-trimethyl-1,6-diisocyanatohexane, tetramethylxylylene diisocyanate (TMXDI) 1-isocyanato-3,3,5-trimethyl-5-isocyanatomethylcyclohexane (isophorone diisocyanate, IPDI), 1-isocyanato-1-methyl-4(3)-isocyanatomethylcyclohexane, dicyclohexylmethane 2,4'-diisocyanate and/or 4,4'-diisocyanate, 1,10-diisocyanatodecane, 1,12-diisocyanatododecane, cyclohexane 1,3- and 1,4-diisocyanate, xylylene diisocyanate isomers, triisocyanatononane (TIN), naphthylene 1,5-diisocyanate, 2,4-diisocyanatotoluene or mixtures thereof with 2,6-diisocyanatotoluene preferably containing, based on mixtures, up to 35% by weight of 2,6-diisocyanatotoluene, 2,2'-, 2,4'-, 4,4'-diisocyanatodiphenylmethane or technical polyisocyanate mixtures of the diphenylmethane series, or any desired mixtures of the polyisocyanates mentioned.

Preference here is given to using aliphatic, cycloaliphatic or araliphatic polyisocyanates selected from the group 1,4-diisocyanatobutane, 1,5-diisocyanatopentane, 1,6-diisocyanatohexane (HDI), 1,5-diisocyanato-2,2-dimethylpentane, 2,2,4- or 2,4,4-trimethyl-1,6-diisocyanatohexane, tetramethylxylylene diisocyanate (TMXDI) 1-isocyanato-3,3,5-trimethyl-5-isocyanatomethylcyclohexane (isophorone diisocyanate, IPDI), 1-isocyanato-1-methyl-4(3)-isocyanatomethylcyclohexane, dicyclohexylmethane 2,4'- and/or 4,4'-diisocyanate, 1,10-diisocyanatodecane, 1,12-diisocyanatododecane, cyclohexane 1,3- and 1,4-diisocyanate, xylylene diisocyanate isomers, triisocyanatononane (TIN), or any desired mixtures of such polyisocyanates.

In principle, it is of course also possible to use mixtures of different polyisocyanate components of the type mentioned above.

In addition to the polyaspartic ester-containing compositions A1 and optionally A2, the preferably two-component coating composition of the invention may comprise further components (components C) that are reactive toward isocyanate groups.

These may, for example, be low-molecular-weight polyols in the molecular weight range from 62 to 300 g/mol, for example ethylene glycol, propylene glycol, trimethylolpropane, glycerol or mixtures of these alcohols, or polyhydroxy compounds having a molecular weight above 300 g/mol, preferably above 400 g/mol, more preferably between 400 and 8000 g/mol. Such polyhydroxyl compounds are in particular those having 2 to 6, preferably 2 to 3, hydroxyl groups per molecule and are selected from the group consisting of ether, ester, thioether, carbonate and polyacrylate polyols and mixtures of such polyols.

The preferably two-component coating compositions of the invention may further comprise auxiliaries and additives (component D). These are the auxiliaries and additives customary in coating technology, such as inorganic or organic pigments, other organic light stabilizers, radical scavengers, paint additives such as dispersants, leveling agents, thickeners, defoaming agents and other auxiliaries, bonding agents, fungicides, bactericides, stabilizers or inhibitors, catalysts and solvents.

The ratio of isocyanate groups in polyisocyanate component B to isocyanate-reactive groups in components A1, A2, and C is preferably 0.5:1.0 to 3.0:1.0. Particular preference is given to a ratio of 0.9:1.0 to 1.5:1.0 Very particular preference is given to a ratio of 1.05:1.0 to 1.25:1.0

The coating composition of the invention is preferably not a foamable or foam-forming composition. The composition is preferably not free-radically polymerizable, especially not photopolymerizable, i.e. the composition does not cure through free-radical processes, especially not through free-radical polymerization processes initiated by actinic radiation.

The coating compositions of the invention are produced by methods known per se in paint and coatings technology.

A preferred production method for a two-component coating composition is described below:

An isocyanate-reactive (R) and an isocyanate-containing component (H) are first prepared separately by mixing the respective isocyanate-reactive components A1 and optionally A2 and optionally C and by mixing the respective polyisocyanate components B. The auxiliaries and additives D1 and D2 are preferably admixed with the isocyanate-reactive component R. The components R and H thus produced are not mixed until immediately before or during application. When mixing takes place before application, it should be noted that the reaction of the constituents commences immediately after mixing. The rate of the reaction varies according to the choice of components and additives. The processing time within which the composition must be applied is also known as the pot life and is defined as the time from mixing of the components until doubling of the initial viscosity and/or flow time (determined according to DIN EN ISO 2431:2012-03, but using a DIN 4 flow cup); depending on the choice of components, this is within a range from 1 minute to 24 hours. The pot life is determined by methods known to those skilled in the art.

The invention also relates to a process for coating a substrate that comprises at least the following steps:
  i) applying the two-component coating composition of the invention to at least part of a substrate to be coated and
  ii) curing the coating composition from step i).

The substrates may have already been coated wholly or partly with one or more coating layers. These coating layers may still be uncured or wet, partly cured or fully cured; the further coating layers on the substrate are preferably partly cured or fully cured. Examples of coating layers are priming coats, primers, fillers, spackling coats, basecoats, or substrates that have already been fully painted and are being recoated after possible pretreatment such as sanding or plasma activation.

The coating compositions of the invention are preferably used in the fields of corrosion protection, initial coating of automobiles, refinishing of automobiles, coatings for large vehicles, coatings for plastics, general industrial coatings, coatings for floors, and/or for wood/furniture.

EXPERIMENTAL PART

Raw Materials and Substrates:

Desmophen NH 1220: an amino-functional co-reactant having an amine value of 240-248 mg KOH/g, a viscosity (25° C.) of ≤100 mPa·s, and a color index (Hazen) of ≤250, manufacturer: Covestro.

Desmophen NH 1420: an amino-functional co-reactant having an amine value of 199-203 mg KOH/g, a viscosity (25° C.) of 900-2000 mPa·s, and a color index (Hazen) of ≤250, manufacturer: Covestro.

Desmodur N 3900: A low-viscosity HDI trimer having approx. 23.5% NCO, a viscosity (25° C.) of approx. 730 mPa·s, and ≤0.25% free HDI, manufacturer: Covestro.

Solvents: Solvesso 100, 1-methoxy-2-propyl acetate (MPA), ethyl acetate (EA), butyl acetate (BA), acetone (Ac), and xylene (Xy), Azelis, Germany.

Tetrahydrofurandimethanamine, Merck, Germany.

3S,3aR,6S,6aR-Hexahydrofuro[3,2-b]furan-3,6-diamine Merck, Germany.

[3S,3aR,6S,6aR-6-(Aminomethyl)-hexahydrofuro[3,2-b]furan-3-yl]-methanamine Merck, Germany.

Diethyl maleate: Aldrich, Germany.

3R,3aR,6S,6aR-Hexahydrofuro[3,2-b]furan-3,6-diamine was prepared by the method described in *ChemSusChem* 2011, 4, 1823-1829.

Methods:

Dimethyl fumarate contents were quantitatively determined using a GC method with internal standard. An Agilent 6890 gas chromatograph with a standard GC capillary (100% polysiloxane phase) and FID detector were used. The injector temperature (split outlet) was 180° C.; helium was used as the carrier gas. The quantitation limit of this method was 300 ppm.

GC-MS analyses were carried out using an Agilent 6890 gas chromatograph and Agilent 5973 mass spectrum detector with standard ionization (electron impact) at 70 eV, a standard GC capillary (100% polysiloxane phase), and split injection at an injector temperature of 250° C. Evaluation of the gas chromatograms was in area-%.

All viscosity measurements were carried out using a Physica MCR 51 rheometer from Anton Paar Germany GmbH (DE) in accordance with DIN EN ISO 3219:1994-10 at 23° C.

Hazen color index values were determined on a Lico 400 colorimeter from Hach Lange GmbH (Germany) in accordance with DIN EN ISO 6271:2016-05

Amine values were determined titrimetrically in accordance with EN ISO 9702:1998 (perchloric acid method) with the exception that the results were expressed as the amine value. The amine value in mg KOH/g was calculated according to the following equation:

$$AA\ AAA\ AAAAA = \frac{(A-A)A5.61}{A}$$

a=Volume of perchloric acid used in the main test, in milliliters, concentration c=0.1 mol/l (included in factor 5.61);

b=Volume of perchloric acid used in the blank test, in milliliters, concentration c=0.1 mol/l (included in factor 5.61);

W=Weight of sample, in grams

The gel time was determined using a Tecam gelation timer from Techne Corp. This method is used to determine the time interval from addition of the curing agent until gelation of the paint, as a measure of the reactivity of the system.

Drying was determined in accordance with DIN EN ISO 9117-5:2012-11 on glass.

Solvent stabilities were determined in accordance with DIN EN ISO 4628-1:2016-07. The solvent stabilities test was carried out using the solvents xylene (also abbreviated hereinafter to "Xy"), methoxypropyl acetate (also abbreviated hereinafter to "MPA"), ethyl acetate (also abbreviated hereinafter to "EA"), and acetone (also abbreviated hereinafter to "Ac"). The contact time was 5 min in each case. The test specimens were made in accordance with the standard cited. The test surface is assessed visually and by scratching, using the following classification: 0=no change apparent; 1=swelling ring, hard surface, only visible change; 2=swelling ring, slight softening; 3=distinct softening (possibly slight blistering); 4=significant softening (possibly severe blistering), can be scratched through to the substrate; 5=coating completely destroyed without outside influence.

König pendulum damping was determined in accordance with DIN EN ISO 1522: 2007-04 on glass plates. The dry film thickness was 45-52 µm for all films.

The cross-cut test was carried out in accordance with DIN EN ISO 2409:2006-13.

The gloss at 20° of the coatings obtained was measured reflectometrically in accordance with DIN EN ISO 2813: 2015-02.

Scratching—crockmeter:

The coating material is scratched using a crockmeter in accordance with DIN EN ISO 105-X12:2016-11. The coated substrate is positioned parallel to the direction of the friction finger. At a frequency of one cycle per second, a straight-line rubbing movement is performed on the dry sample 20 times over a distance of 104±3 mm, this comprising 10 sets of back and forth movements at a downward force of 9±0.2 N. The gloss of the specimen is then determined reflectometrically.

Reflow:

The reflow describes the recovery of a scratched coating surface, based on the gloss value, after thermal stress. A coating is scratched by dry scratching (crockmeter). The residual gloss is determined after the scratching cycle. The coating is placed in the oven at 60° C. for 2 h and the gloss is then determined according to the procedure described above. The reflow is reported in percent, i.e. the ratio of residual gloss after heat-treatment to gloss before scratching.

Weathering:

CAM 180:

The accelerated weathering studies in the presence of UV radiation were carried out in accordance with SAE J2527. The test plates were checked every 250 h.

UV-A test:

The UV-A tests of the coating materials were carried out in accordance with DIN EN ISO 16474-3:2014-03 (cycle 1). The test plates were checked every 250 h.

Calculation of the b value and delta E:

The delta E value can be calculated from the L, a, and b values determined in the Lab color space in accordance with DIN ISO/CIE 11664-4:2019-04 using a Dr. Lange Micro Color II.

Syntheses of the Polyaspartic Esters (PAEs) of the Invention

PAE 1:

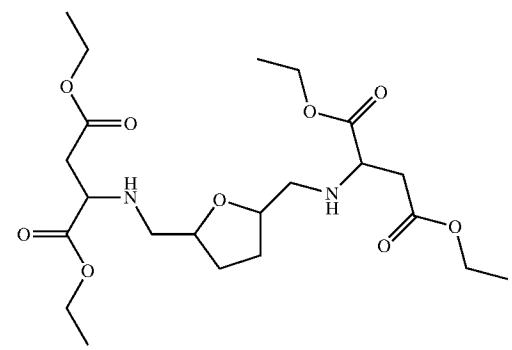 [SMILES: CCOC(=O)CC(NCC1CCC(CNC(CC(=O)OCC)C(=O)OCC)O1)C(=O)OCC]

Prepared using tetrahydrofurandimethanamine

PAE 2:

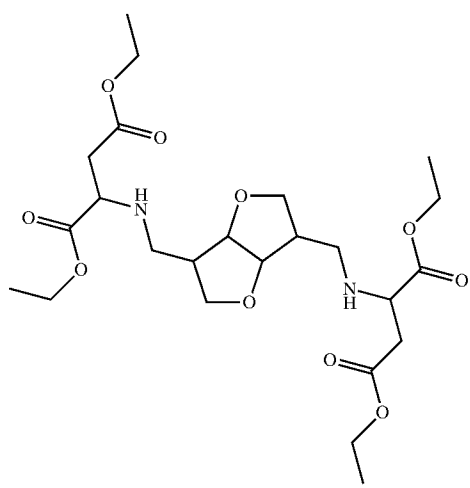 [SMILES: CCOC(=O)CC(NCC1COC2C(CNC(CC(=O)OCC)C(=O)OCC)COC12)C(=O)OCC]

Prepared using [3S,3aR,6S,6aR-6-(aminomethyl)-hexahydrofuro[3,2-b]furan-3-yl]-methanamine.

PAEs 3 and 4:

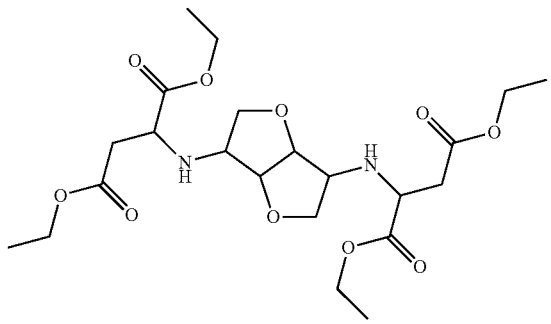 [SMILES: CCOC(=O)CC(NC1COC2C(NC(CC(=O)OCC)C(=O)OCC)COC12)C(=O)OCC]

Prepared using two isomers: PAE 3: 3S,3aR,6S,6aR-hexahydrofuro[3,2-b]furan-3,6-diamine and PAE 4: 3R,3aR,6S,6aR-hexahydrofuro[3,2-b]furan-3,6-diamine Polyaspartic Ester PAE 1 (of the Invention)

340.2 g of tetrahydrofurandimethanamine (rel-((2R,5S)-tetrahydrofuran-2,5-diyl)dimethanamine, cis) was initially charged at 30° C. under dry nitrogen and with stirring. To this was added dropwise 900.0 g of diethyl maleate, ensuring that the temperature did not rise above 60° C. At the end of the addition, the temperature was adjusted to 45° C. and the mixture was stirred at 45° C. for 1 hour. The mixture was then stored at 23° C. for 1 week. A light-colored product was obtained that had the following material data:

| Diethyl fumarate (GC) | 1.74% by weight |
|---|---|
| Viscosity | 170 mPas |
| Color index | 22 APHA |
| Amine value | 234 mg KOH/g |

Polyaspartic Ester PAE 3 (of the Invention)

72.08 g of (3S,3aR,6S,6aR)-hexahydrofuro[3,2-b]furan-3,6-diamine was initially charged under dry nitrogen and heated to 90° C. with stirring. To this was added dropwise 172.0 g of diethyl maleate, ensuring that the temperature did not remain at 90° C. At the end of the addition, the temperature was adjusted to 60° C. and the mixture was stirred at 60° C. for 2 hours. The mixture was then stored at 23° C. for 20 weeks. A product was obtained that had the following material data:

| Diethyl fumarate (GC) | 4.82% by weight |
|---|---|
| Amine value | 240 mg KOH/g |
| Viscosity | 1010 mPas |

Polyaspartic Ester PAE 2 (of the Invention)

86.11 g of [(3S,3aR,6S,6aR)-6-(aminomethyl)-hexahydrofuro[3,2-b]furan-3-yl]methanamine was initially charged at 30° C. under dry nitrogen and with stirring. To this was added dropwise 172.0 g of diethyl maleate, ensuring that the temperature did not rise above 60° C. At the end of the addition, the temperature was adjusted to 45° C. and the mixture was stirred at 45° C. for one hour. The mixture was then stored at 23° C. for 4 weeks. A product was obtained that had the following material data:

| Diethyl fumarate (GC) | 5.35% by weight |
|---|---|
| Amine value | 253 mg KOH/g |
| Viscosity | 850 mPas |

Polyaspartic Ester PAE 4 (of the Invention)

72.08 g of (3R,3aR,6S,6aR)-hexahydrofuro[3,2-b]furan-3,6-diamine was initially charged under dry nitrogen and heated to 90° C. with stirring. To this was added dropwise 172.0 g of diethyl maleate, ensuring that the temperature did not rise above 90° C. At the end of the addition, the temperature was adjusted to 60° C. and the mixture was stirred at 60° C. for 2 hours. The mixture was then stored at 23° C. for 8 weeks. A product was obtained that had the following material data:

| Diethyl fumarate (GC) | 8.75% by weight |
|---|---|
| Amine value | 226 mg KOH/g |
| Viscosity | 420 mPas |

Preparation of the Coatings:

TABLE 1

| | Weights in grams | | | | | |
|---|---|---|---|---|---|---|
| | 1 (comp.) | 2 (comp.) | 3 | 4 | 5 | 6 |
| Coating base: | | | | | | |
| PAE 1 | | | 100.00 | | | |
| PAE 2 | | | | 100.00 | | |
| PAE 3 | | | | | 50.00 | |
| PAE 4 | | | | | | 100 |
| Desmophen NH 1220 | 100.00 | 35.00 | | | | |
| Desmophen NH 1420 | | 65.00 | | | | |
| Curing agent | | | | | | |
| Desmodur N 3900 | 76.50 | 68.93 | 75.18 | 69.30 | 36.64 | 73.28 |
| Total | 176.50 | 168.93 | 175.18 | 169.30 | 86.64 | 173.28 |
| Ratio (NCO/NH) | 1.0 | 1.0 | 1.0 | 1.0 | 1.0 | 1.0 |
| Gel time in min | 1 min. | 11 min | 5 min | 4 min | 162 min | 187 min |

Mixing of the coating base with the curing agent and application:

The components A (coating base) and B (curing agent) mentioned above were in each case combined and mixed thoroughly. The mixtures were then applied to the glass plates using an applicator frame (wet layer thickness 90 μm) and dried at room temperature (23° C.). Brilliant, high-gloss coatings with a dry film thickness of 45 to 52 μm were obtained. An overview of the coating properties determined for the coatings is shown in Tables 2 to 4.

Solvent Resistance:

Measured on clearcoats on glass plate. Assessment: 0-5 (0=film coating unchanged; 5=fully dissolved)

As can be seen from the table, coatings based on the polyaspartic esters of the invention have considerably better solvent resistance and considerably better reflow behavior than coatings based on polyaspartic esters of the prior art.

Weathering Tests:

i) Gloss Development:

TABLE 2

| Example | 1 (comp.) | 2 (comp.) | 3 | 4 | 5 | 6 |
|---|---|---|---|---|---|---|
| Dry film thickness (μm) | 50 | 45 | 45 | 52 | 50 | 52 |
| Pendulum hardness | | | | | | |
| after 1 day | 52 | 174 | 194 | 148 | 170 | 136 |
| after 7 days | | | 191 | 171 | 200 | 202 |
| Solvent resistance after 1 day | | | | | | |
| xylene (1/5 min) | 2/2 | 2/2 | 1/1 | 1/2 | 1/1 | 2/3 |
| MPA (1/5 min) | 2/3 | 2/2-3 | 1/2 | 1/1 | 1/2 | 2/3 |
| ethyl acetate (1/5 min) | 2-3/5 | 3/5 | 2/3 | 2/3 | 2/4 | 4/4 |
| acetone (1/5 min) | 5/5 | 5/5 | 3/4 | 4/4 | 3/4 | 4/5 |
| Solvent resistance after 7 days | | | | | | |
| xylene (1/5 min) | | | 1/1 | 1/1 | 1/2 | 1/1 |
| MPA (1/5 min) | | | 1/2 | 1/1 | 2/2 | 1/1 |
| ethyl acetate (1/5 min) | | | 1/3 | 2/3 | 2/5 | 2/3 |
| acetone (1/5 min) | | | 3/4 | 3/3 | 4/5 | 3/3 |
| Scratch resistance - Crockmeter (dry scratching) | | | | | | |
| Gloss 20° Start | | 86 | 84 | 86 | n.d. | n.d. |
| After scratching | | 5 | 15 | 13 | n.d. | n.d. |
| 2 h 60° C. oven | | 21 | 63 | 40 | n.d. | n.d. |
| Rel. gloss retention | | 24.4% | 75% | 46.5% | n.d. | n.d. |

TABLE 3

| h | 0 | 250 | 500 | 750 | 1000 | 1250 | 1500 | 1750 | 2000 |
|---|---|---|---|---|---|---|---|---|---|
| | | | | | Gloss development 20° | | | | |
| | | | | | UVA | | | | |
| 1 | 88 | 93 | 93 | 91 | 89 | 89 | 82 | 87 | 87 |
| 3 | 89 | 76 | 93 | 90 | 88 | 88 | 88 | 90 | 89 |
| 2 (comp.) | 88 | 93 | 94 | 92 | 90 | 88 | 86 | 88 | 90 |
| | | | | | CAM 180 | | | | |
| 1 | 87 | 88 | 88 | 82 | 87 | 89 | 83 | 86 | 86 |
| 3 | 85 | 90 | 91 | 88 | 89 | 87 | 89 | 86 | 0 |
| 2 (comp.) | 85 | 76 | 68 | 78 | 87 | 0 | | | |

As can be seen from Table 3, the gloss development of the coatings of the invention is comparable to coatings based on polyaspartic esters of the prior art.

ii) Resistance to Yellowing:

TABLE 4

| | 0 | 250 | 500 | 750 | 1000 | 1250 | 1500 | 1750 | 2000 | 0 | 250 | 500 | 750 | 1000 | 1250 | 1500 | 1750 | 2000 |
|---|---|---|---|---|---|---|---|---|---|---|---|---|---|---|---|---|---|---|
| h | | | | | b value | | | | | | | | | Delta E | | | | |
| | | | | | | | | | UVA: | | | | | | | | | |
| 1 | −0.9 | 0.6 | 1.3 | 3.2 | 4.7 | 5.5 | 5.6 | 5.7 | 6 | 0 | 1.8 | 2.5 | 4.4 | 6 | 6.7 | 6.9 | 7 | 7.4 |
| 3 | 8.9 | 13.6 | 13 | 13.5 | 12.6 | 12.6 | 12.6 | 12.2 | 11.3 | 0 | 5.4 | 5 | 5.4 | 5.6 | 6.1 | 6.2 | 5.8 | 5.5 |
| 2 | −0.4 | 2.1 | 1.9 | 3.3 | 5.2 | 6.8 | 7.8 | 8.4 | 9 | 0 | 2.6 | 2.5 | 3.9 | 5.8 | 7.5 | 8.5 | 9.1 | 9.8 |
| | | | | | | | | | CAM 180: | | | | | | | | | |
| 1 | −0.4 | 1.2 | 2.6 | 3 | 3 | 2.9 | 2.8 | 2.8 | 2.9 | 0 | 1.7 | 3.2 | 3.6 | 3.6 | 3.5 | 3.4 | 3.4 | 3.5 |
| 3 | 4.9 | 3.3 | 3.2 | 3.1 | 3.3 | 3.8 | 3.4 | 3.2 | 3.2 | 0 | 0.6 | 0.4 | 1.2 | 0.7 | 0.8 | 0.8 | 0.9 | |
| 2 | −0.3 | 0.9 | 1.3 | 2.7 | 2.7 | 3.4 | 2.1 | 2.6 | 4.6 | 0 | 1.3 | 1.8 | 3.2 | 3.4 | 4.4 | 2.6 | 3.2 | 5.5 |

As can be seen from Table 4, the coatings of the invention exhibit considerably better resistance to yellowing than corresponding polyaspartate-based coatings of the prior art.

The invention claimed is:

1. A composition A1 comprising one or more polyaspartic esters of the general formula (I)

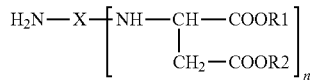
(I)

in which
- X is an m-valent organic radical obtained by removing the primary amino groups from cyclic ethers, said ethers being monocycles or fused bicycles based on monocyclic ethers and which on at least 2 of a ring carbon atoms bear a group selected from primary amino group and aliphatically attached primary amino group, where
- R1 and R2 are identical or different organic radicals each having 1 to 18 carbon atoms and
- m is an integer >1, and optionally one or more polyaspartic esters having a primary amino group of the general formula (II)

(II)

in which
- n is m−1 and
- X and the radicals R1 and R2 are as defined above, wherein the cyclic ethers from which X is derived and which on at least 2 of the ring carbon atoms bear a group selected from primary amino group and aliphatically attached primary amino group having the compounds of formula V

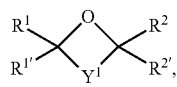
(V)

are monocycles or bicycles according to the following general formulas III and IV:

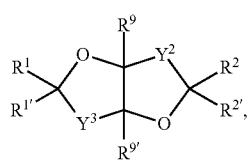

Formula III

Formula IV where $Y^1$ is $Y^1a$, $Y^1b$, $Y^1c$, $Y^1d$, $Y^1e$, $Y^1f$, $Y^1g$, $Y^1h$ or, $Y^1i$:

$Y^1a$

$Y^1b$

$Y^1c$

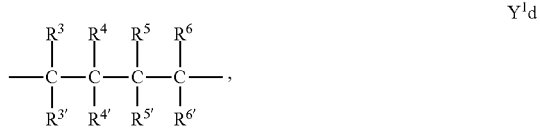
$Y^1d$

$Y^1e$

$Y^1f$

$Y^1g$

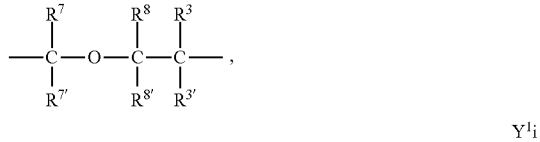
$Y^1h$

$Y^1i$ and $Y^2$ is $Y^2a$, $Y^2b$, $Y^2c$, $Y^2d$, $Y^2e$, or $Y^2f$:

$Y^2a$

$Y^2b$

-continued $Y^2c$
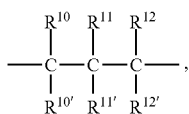

$Y^2d$
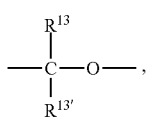

$Y^2e$
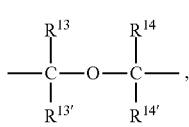

$Y^2f$
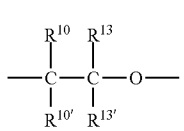

and $Y^3$ is $Y^3a$, $Y^3b$, $Y^3c$, $Y^3d$, $Y^3e$, or $Y^3f$:

$Y^3a$
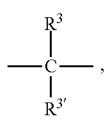

$Y^3b$
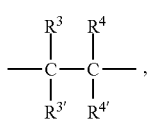

$Y^3c$
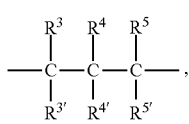

$Y^3d$
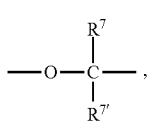

$Y^3e$
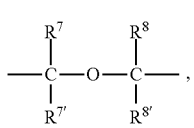

$Y^3f$
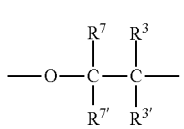

and $R^1$, $R^2$, $R^7$, $R^8$, $R^{13}$, $R^{14}$ are independently: (i) an alkylene group having 1 to 6 carbon atoms, wherein one C-atom of the alkylene group is attached to a $NH_2$-group; (ii) hydrogen; or (iii) organic radicals, the latter being saturated or unsaturated, linear or branched, aliphatic or cycloaliphatic or optionally substituted aromatic or araliphatic monovalent radicals having up to 18 carbon atoms, which may optionally contain heteroatoms from the series oxygen, sulfur and nitrogen, and $R^3$, $R^4$, $R^5$, $R^6$, $R^{10}$, $R^{11}$, $R^{12}$ are independently: (i) a linear or branched alkylene group having 1 to 6 carbon atoms, wherein one C-atom of the alkylene group is attached to a $NH_2$-group; (ii) a $NH_2$-group; (iii) a hydrogen; or (iv) organic radicals, the latter being saturated or unsaturated, linear or branched, aliphatic or cycloaliphatic or optionally substituted aromatic or araliphatic monovalent radicals having up to 18 carbon atoms, which may optionally contain heteroatoms from the series oxygen, sulfur and nitrogen, where in the case of formula III at least 2 of the radicals $R^1$ to $R^8$ comprise a $NH_2$ group, and in the case of formula IV at least one of the radicals $R^1$ to $R^8$ comprise a $NH_2$ group and at least one of the radicals $R^{10}$ to $R^{14}$ comprise a $NH_2$ group, and $R^9$ and $R^{9'}$ are independently H or a methyl radical, and $R^{1'}$ to $R^{8'}$, and $R^{10'}$ to $R^{14'}$ are independently hydrogen or organic radicals, the latter being saturated or unsaturated, linear or branched, aliphatic or cycloaliphatic or optionally substituted aromatic or araliphatic monovalent radicals having up to 18 carbon atoms, which may optionally contain heteroatoms from the series oxygen, sulfur and nitrogen.

2. A process for producing compositions A1 comprising one or more polyaspartic esters of the general formula (I)

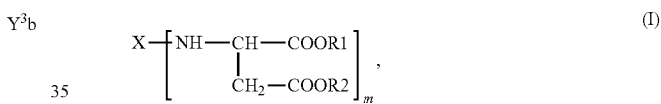

in which

X is an m-valent organic radical obtained by removing the primary amino groups from cyclic ethers, said ethers being monocycles or fused bicycles based on monocyclic ethers and which on at least 2 of a ring carbon atoms bear a group selected from primary amino group and aliphatically attached primary amino group, where R1 and R2 are identical or different organic radicals each having 1 to 18 carbon atoms and m is an integer >1, and optionally one or more polyaspartic esters having a primary amino group of the general formula (II)

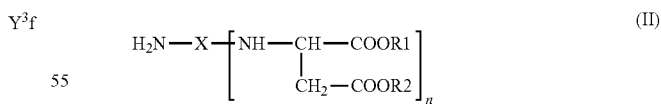

in which n is m−1 and

X and the radicals R1 and R2 are as defined above, by reacting polyamines of the general formula (V)

in which X and m are as defined above,
with compounds of the general formula (VI)

$$R1OOC—CH=CH—COOR2 \quad (VI)$$

where R1 and R2 are as defined above,
wherein the cyclic ethers from which X is derived and which on at least 2 of the ring carbon atoms bear a group selected from primary amino group and aliphatically attached primary amino group having the compounds of formula V, are monocycles or bicycles according to the following general formulas III and IV:

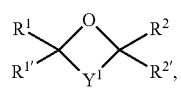

Formula III

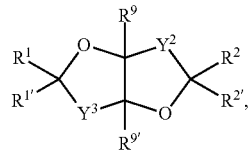

Formula IV where $Y^1$ is $Y^1a$, $Y^1b$, $Y^1c$, $Y^1d$, $Y^1e$, $Y^1f$, $Y^1g$, $Y^1h$ or, $Y^1i$:

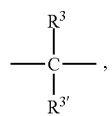

$Y^1a$

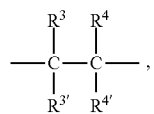

$Y^1b$

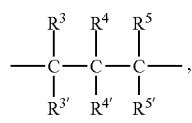

$Y^1c$

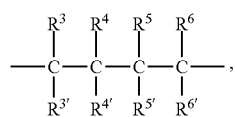

$Y^1d$

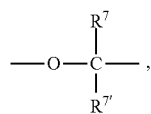

$Y^1e$

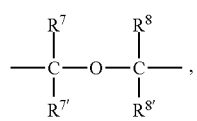

$Y^1f$

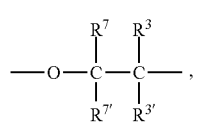

$Y^1g$

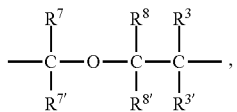

$Y^1h$

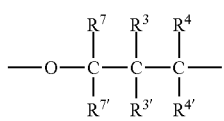

$Y^1i$ and $Y^2$ is $Y^2a$, $Y^2b$, $Y^2c$, $Y^2d$, $Y^2e$, or $Y^2f$:

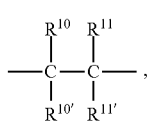

$Y^2a$

$Y^2b$

$Y^2c$

$Y^2d$

$Y^2e$

$Y^2f$ and $Y^3$ is,

$Y^3a$

$Y^3b$

$Y^3c$

-continued

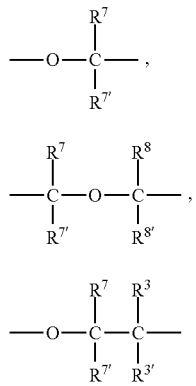

$Y^3d$ $Y^3e$ $Y^3f$ and $R^1, R^2, R^7, R^8, R^{13}, R^{14}$ are independently: (i) an alkylene group having 1 to 6 carbon atoms, wherein one C-atom of the alkylene group is attached to a $NH_2$-group; (ii) hydrogen; or (iii) organic radicals, the latter being saturated or unsaturated, linear or branched, aliphatic or cycloaliphatic or optionally substituted aromatic or araliphatic monovalent radicals having up to 18 carbon atoms, which may optionally contain heteroatoms from the series oxygen, sulfur and nitrogen, and $R^3, R^4, R^5, R^6, R^{10}, R^{11}, R^{12}$ are independently: (i) a linear or branched alkylene group having 1 to 6 carbon atoms, wherein one C-atom of the alkylene group is attached to a $NH_2$-group; (ii) a $NH_2$-group; (iii) a hydrogen; or (iv) organic radicals, the latter being saturated or unsaturated, linear or branched, aliphatic or cycloaliphatic or optionally substituted aromatic or araliphatic monovalent radicals having up to 18 carbon atoms, which may optionally contain heteroatoms from the series oxygen, sulfur and nitrogen, where in the case of formula III at least 2 of the radicals $R^1$ to $R^8$ comprise a $NH_2$ group, and in the case of formula IV at least one of the radicals $R^1$ to $R^8$ comprise a $NH_2$ group and at least one of the radicals $R^{10}$ to $R^{14}$ comprise a $NH_2$ group, and $R^9$ and $R^{9'}$ are independently H or a methyl radical, and $R^{1'}$ to $R^{8'}$, and $R^{10'}$ to $R^{14'}$ are independently hydrogen or organic radicals, the latter being saturated or unsaturated, linear or branched, aliphatic or cycloaliphatic or optionally substituted aromatic or araliphatic monovalent radicals having up to 18 carbon atoms, which may optionally contain heteroatoms from the series oxygen, sulfur and nitrogen.

3. The composition A1 as claimed in claim 1, wherein the alkylene groups having 1 to 6 carbon atoms are $CH_2$, $CH_2$—$CH_2$, $CH_2$—$CH_2$—$CH_2$ or $CH_2$—$CH_2$—$CH_2$—$CH_2$.

4. The composition A1 as claimed in claim 1, wherein the radicals $R^1, R^2, R^3, R^4, R^5, R^6, R^7, R^8, R^{10}, R^{11}, R^{12}, R^{13}, R^{14}$, where they are hydrogen or organic radicals, are independently hydrogen and/or alkyl radicals each having 1 to 8 carbon atoms.

5. The composition A1 as claimed in claim 1, in which X was obtained by removing the primary amino groups from cyclic ethers that are based on starting materials obtained in a biobased manner.

6. The composition A1 as claimed in claim 1 in a mixture with a further polyaspartic ester containing composition different from the composition A1.

7. A coating composition, comprising
a) at least one polyaspartic ester-containing composition A1 as claimed in claim 1,
b) at least one polyisocyanate component B,
c) optionally one or more components C different from A1 and reactive toward isocyanate groups,
(d) optionally auxiliaries and additives (component D).

8. A process for coating a substrate that comprises at least the following steps:
i) applying a coating composition as claimed in claim 7 to at least part of a substrate to be coated; and
ii) curing the coating composition from step i).

9. A substrate coated with a coating obtained in accordance with a process as claimed in claim 8.

10. The process for producing the composition A1 as claimed in claim 2 wherein the alkylene groups having 1 to 6 carbon atoms are $CH_2$, $CH_2$—$CH_2$, $CH_2$—$CH_2$—$CH_2$ or $CH_2$—$CH_2$—$CH_2$—$CH_2$.

11. The process for producing the composition A1 as claimed in claim 2, wherein the radicals $R^1, R^2, R^3, R^4, R^5, R^6, R^7, R^8, R^{10}, R^{11}, R^{12}, R^{13}, R^{14}$, where they are hydrogen or organic radicals, are independently hydrogen and/or alkyl radicals each having 1 to 8 carbon atoms.

12. The process for producing the composition A1 as claimed in claim 2, in which X was obtained by removing the primary amino groups from the cyclic ethers that are based on starting materials obtained in a biobased manner.

13. The coating composition of claim 7, wherein the composition is a two-component coating composition.

14. The composition A1 according to claim 1, wherein in formula III $Y^1$ is
i) $Y^1a$, wherein $R^1$ and $R^2$ are each $CH_2$—$NH_2$, and $R^{1'}$, $R^{2'}$, $R^3$, and $R^{3'}$ are independently organic radicals having up to 18 carbon atoms or H,
ii) $Y^1b$, wherein two of $R^1, R^2, R^3$ and $R^4$ are $CH_2$—$NH_2$, and two of $R^1, R^2, R^3$ and $R^4$ and also $R^{1'}$ to $R^{4'}$ are independently organic radicals having up to 18 carbon atoms or H,
or $R^3$ and $R^4$ are $NH_2$, and $R^1, R^{1'}, R^2, R^{2'}, R^{3'}$, and $R^{4'}$ are independently organic radicals having up to 18 carbon atoms or H,
iii) $Y^1c$, wherein two of $R^1, R^2, R^3$, and $R^5$ are $CH_2$—$NH_2$, and two of $R^1, R^2, R^3$, and $R^5$ and also $R^{1'}$ to $R^{5'}$ and $R^4$ are independently organic radicals having up to 18 carbon atoms or H,
or $R^3$ and $R^4$ are $NH_2$, and $R^1, R^2, R^5$ and also $R^{1'}$ to $R^{5'}$ are independently organic radicals having up to 18 carbon atoms or H,
or $R^3$ and $R^5$ are $NH_2$, and $R^1, R^2, R^4$ and also $R^{1'}$ to $R^{5'}$ are independently organic radicals having up to 18 carbon atoms or H,
or $R^1$ is $CH_2$—$NH_2$ and one of $R^3, R^4$ and $R^5$ is $NH_2$, and two of $R^3, R^4$ and $R^5$, and also $R^{1'}$ to $R^{5'}$ and $R^2$, are independently organic radicals having up to 18 carbon atoms or H,
iv) $Y^1d$, wherein two of $R^1, R^2, R^3$, and $R^6$ are $CH_2$—$NH_2$, and two of $R^1, R^2, R^3$, and $R^6$, and also $R^4, R^5$, and $R^{1'}$ to $R^{6'}$ are independently organic radicals having up to 18 carbon atoms or H,
or $R^3$ and $R^6$ are $NH_2$, and $R^1, R^2, R^4, R^5$ and $R^{1'}$ to $R^{6'}$ are independently organic radicals having up to 18 carbon atoms or H,
or $R^1$ is $CH_2$—$NH_2$ and $R^3$ or $R^6$ is $NH_2$, and one of $R^3$ and $R^6$, and also $R^{1'}$ to $R^{5'}$ and $R^2$ are independently organic radicals having up to 18 carbon atoms or H, v) $Y^1$e, wherein two of $R^1$, $R^2$, and $R^7$ are $CH_2-NH_2$, and one of $R^1$, $R^2$, and $R^7$, and also $R^{1'}$, $R^{2'}$, and $R^{7'}$ are independently organic radicals having up to 18 carbon atoms or H, vi) $Y^1$f, wherein two of $R^1$, $R^2$, $R^7$, and $R^8$ are $CH_2-NH_2$, and two of $R^1$, $R^2$, $R^7$, and $R^8$, and also $R^{1'}$, $R^{2'}$, $R^{7'}$, and $R^{8'}$ are independently organic radicals having up to 18 carbon atoms or H, vii) $Y^1$g, wherein two of $R^1$, $R^2$, $R^3$, and $R^7$ are $CH_2-NH_2$, and two of $R^1$, $R^2$, $R^3$, and $R^7$, and also $R^{1'}$, $R^{2'}$, $R^{3'}$, and $R^{7'}$ are independently organic radicals having up to 18 carbon atoms or H, or $R^1$ is $CH_2-NH_2$ and $R^3$ is $NH_2$, and $R^2$, $R^7$, $R^{1'}$, $R^{2'}$, $R^{3'}$, and $R^{7'}$ are independently organic radicals having up to 18 carbon atoms or H, viii) $Y^1$h, wherein two of $R^1$, $R^2$, $R^3$, $R^7$, and $R^8$ are $CH_2-NH_2$, and three of $R^1$, $R^2$, $R^3$, $R^7$, and $R^8$, and also $R^{1'}$, $R^{2'}$, $R^{3'}$, $R^{7'}$, and $R^{8'}$ are independently organic radicals having up to 18 carbon atoms or H, or $R^1$ is $CH_2-NH_2$ and $R^3$ is $NH_2$, and $R^2$, $R^7$, and $R^8$ and also $R^{1'}$, $R^{2'}$, $R^{3'}$, $R^{7'}$, and $R^{8'}$ are independently organic radicals having up to 18 carbon atoms or H, or ix) $Y^1$i, wherein two of $R^1$, $R^2$, $R^3$, $R^4$, and $R^7$ are $CH_2-NH_2$, and three of $R^1$, $R^2$, $R^3$, $R^4$, and $R^7$, and also $R^{1'}$, $R^{2'}$, $R^{3'}$, $R^{4'}$, and $R^{7'}$ are independently organic radicals having up to 18 carbon atoms or H, or $R^1$ is $CH_2-NH_2$ and $R^3$ or $R^4$ is $NH_2$, and $R^3$ or $R^4$, and also $R^2$, $R^7$, $R^{1'}$, $R^{2'}$, $R^{3'}$, $R^{4'}$, and $R^{7'}$ are independently organic radicals having up to 18 carbon atoms or H.

15. The composition A1 according to claim 14, wherein in formula III $Y^1$ is embodiment ii) or iii):

ii) Y1 is $Y^1$b, $R^1$ and $R^2$ are each $CH_2-NH_2$, and $R^3$, $R^4$ and also $R^{1'}$ to $R^{4'}$ are independently organic radicals having up to 18 carbon atoms or H, or $R^3$ and $R^4$ are $CH_2-NH_2$ or $NH_2$, and $R^1$, $R^2$ and also $R^{1'}$ to $R^{4'}$ are independently organic radicals having up to 18 carbon atoms or H, or iii) Y1 is $Y^1$c, $R^1$ and $R^2$ are $CH_2-NH_2$, and $R^3$, $R^4$, $R^5$ and also $R^{1'}$ to $R^{5'}$ are independently organic radicals having up to 18 carbon atoms or H, or $R^3$ and $R^5$ are $CH_2-NH_2$ or $NH_2$, and $R^1$, $R^2$, $R^4$ and also $R^{1'}$ to $R^{5'}$ are independently organic radicals having up to 18 carbon atoms or H.

16. The composition A1 according to claim 14, wherein in formula III $Y^1$ is embodiment ii) or iii):

ii) Y1 is $Y^1$b, $R^1$ and $R^2$ are $CH_2-NH_2$, and $R^3$, $R^4$ and also $R^{1'}$ to $R^{4'}$ are independently a methyl radical or H, or $R^3$ and $R^4$ are $CH_2-NH_2$ or $NH_2$, and $R^1$, $R^2$ and also $R^{1'}$ to $R^{4'}$ are independently a methyl radical or H, or iii) Y1 is $Y^1$c, $R^1$ and $R^2$ are $CH_2-NH_2$, and $R^3$, $R^4$, $R^5$ and also $R^{1'}$ to $R^{5'}$ are independently a methyl radical or H, or $R^3$ and $R^5$ are $CH_2-NH_2$ or $NH_2$, and $R^1$, $R^2$, $R^4$ and also $R^{1'}$ to $R^{5'}$ are independently a methyl radical or H.

17. The composition A1 according to claim 1, wherein the compounds of formula III are oxacyclopentane-2,3-, -2,4-, -2,5- or -3,4-di-methyleneamine or oxacyclohexane-2,3-, -2,4-, -2,5-, -2,6-, -3,4- or -3,5-di-methyleneamine.

18. The composition A1 according to claim 1, wherein in formula IV $Y^2$ and $Y^3$ are a) $Y^2$a and $Y^3$a, $R^2$ is $CH_2-NH_2$ or $R^{10}$ is $CH_2-NH_2$ or $NH_2$ and $R^1$ is $CH_2-NH_2$ or $R^3$ is $CH_2-NH_2$ or $NH_2$, and $R^2$ or $R^{10}$, $R^1$ or $R^3$, and also $R^{1'}$, $R^{2'}$, $R^{3'}$, and $R^{10'}$ are independently methyl, ethyl, propyl, isopropyl, butyl or isobutyl radicals or H, and $R^9$, $R^{9'}$ are independently $CH_3$ or H, b) $Y^2$a and $Y^3$b, $R^2$ is $CH_2-NH_2$ or $R^{10}$ is $CH_2-NH_2$ or $NH_2$ and $R^1$ is $CH_2-NH_2$ or $R^3$ or $R^4$ is $CH_2-NH_2$ or $NH_2$, and $R^2$ or $R^{10}$, at least one of $R^1$, $R^3$, and $R^4$, and also $R^{1'}$, $R^{2'}$, $R^{3'}$, $R^{4'}$, and $R^{10'}$ are independently methyl, ethyl, propyl, isopropyl, butyl or isobutyl radicals or H, and $R^9$, $R^{9'}$ are independently $CH_3$ or H, c) $Y^2$a and $Y^3$d, $R^2$ is $CH_2-NH_2$ or $R^{10}$ is $CH_2-NH_2$ or $NH_2$ and $R^1$ or $R^7$ is $CH_2-NH_2$, and $R^2$ or $R^{10}$, $R^1$ or $R^7$, and also $R^{1'}$, $R^{2'}$, $R^{7'}$, and $R^{10'}$ are independently methyl, ethyl, propyl, isopropyl, butyl or isobutyl radicals or H, and $R^9$, $R^{9'}$ are independently $CH_3$ or H, d) $Y^2$b and $Y^3$b, $R^2$ is $CH_2-NH_2$ or $R^{10}$ or $R^{11}$ is $CH_2-NH_2$ or $NH_2$ and $R^1$ is $CH_2-NH_2$ or $R^3$ or $R^4$ is $CH_2-NH_2$ or $NH_2$, and at least one of $R^2$, $R^{10}$, and $R^{11}$, the at least one of $R^1$, $R^3$, and $R^7$, and also $R^{1'}$, $R^{2'}$, $R^{3'}$, $R^{4'}$, $R^{10'}$, and $R^{11'}$ are independently methyl, ethyl, propyl, isopropyl, butyl or isobutyl radicals or H, and $R^9$, $R^{9'}$ are independently $CH_3$ or H, e) $Y^2$d and $Y^3$d, $R^2$ or $R^{13}$ is $CH_2-NH_2$ and $R^1$ or $R^7$ is $CH_2-NH_2$, and $R^2$ or $R^{13}$, $R^1$ or $R^7$, and also $R^{1'}$, $R^{2'}$, $R^{7'}$, and $R^{13'}$ are independently methyl, ethyl, propyl, isopropyl, butyl or isobutyl radicals or H, and $R^9$, $R^{9'}$ are independently $CH_3$ or H, or f) $Y^2$b and $Y^3$d, $R^2$ is $CH_2-NH_2$ or $R^{10}$ or $R^{11}$ is $CH_2-NH_2$ or $NH_2$ or $R^1$ or $R^7$ is $CH_2-NH_2$, and at least one of $R^2$, $R^{10}$ and $R^{11}$, $R^1$ or $R^7$, and also $R^{1'}$, $R^{2'}$, $R^{7'}$, $R^{10'}$, and $R^{11'}$ are independently methyl, ethyl, propyl, isopropyl, butyl or isobutyl radicals or H, and $R^9$ and $R^{9'}$ are independently $CH_3$ or H.

19. The composition A1 according to claim 18, wherein in formula IV $Y^2$ and $Y^3$ are embodiments a), b) or d).

20. The composition A1 according to claim 1, wherein the compound of formula IV is selected from the group consisting of 3R,3aR,6R,6aR-hexahydrofuro[3,2-b]furan-3,6-diamine; 3R,3aR,6S,6aR-hexahydrofuro[3,2-b]furan-3,6-diamine; 3S,3aR,6S,6aR-hexahydrofuro[3,2-b]furan-3,6-diamine; [3R,3aR,6R,6aR-6-(aminomethyl)-hexahydrofuro[3,2-b]furan-3-yl]methanamine; [3R,3aR,6S,6aR-6-(aminomethyl)-hexahydrofuro[3,2-b]furan-3-yl]methanamine; [3S,3aR,6S,6aR-6-(aminomethyl)-hexahydrofuro[3,2-b]furan-3-yl]methanamine; and mixtures thereof.

* * * * *